United States Patent
Maschke

(10) Patent No.: US 7,720,528 B2
(45) Date of Patent: May 18, 2010

(54) CATHETER FOR INSERTING INTO A VESSEL

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 1488 days.

(21) Appl. No.: 11/031,798

(22) Filed: Jan. 7, 2005

(65) Prior Publication Data

US 2005/0192496 A1  Sep. 1, 2005

(30) Foreign Application Priority Data

Jan. 9, 2004  (DE)  ........................ 10 2004 001 498

(51) Int. Cl.
*A61B 5/00* (2006.01)
*A61F 2/06* (2006.01)

(52) U.S. Cl. ........................ 600/476; 600/116; 623/1.12

(58) Field of Classification Search ................. 600/473, 600/476, 462–470, 423–425, 478; 606/159, 606/170, 191–194; 623/1.13, 1.12, 1.11, 623/1.16; 604/50–54, 96

See application file for complete search history.

(56) References Cited

U.S. PATENT DOCUMENTS

| | | | |
|---|---|---|---|
| 5,749,848 A * | 5/1998 | Jang et al. | 604/509 |
| 5,830,145 A | 11/1998 | Tenhoff | |
| 5,971,968 A * | 10/1999 | Tu et al. | 604/264 |
| 6,221,049 B1 | 4/2001 | Selmon et al. | |
| 6,503,242 B1 * | 1/2003 | Elsberry | 604/508 |
| 6,899,729 B1 * | 5/2005 | Cox et al. | 623/1.13 |
| 7,258,697 B1 * | 8/2007 | Cox et al. | 623/1.16 |
| 2002/0019644 A1 * | 2/2002 | Hastings et al. | 606/159 |
| 2002/0077647 A1 * | 6/2002 | Snow et al. | 606/170 |
| 2003/0199767 A1 * | 10/2003 | Cespedes et al. | 600/473 |
| 2004/0082861 A1 * | 4/2004 | Gruhl | 600/466 |
| 2004/0097804 A1 * | 5/2004 | Sobe | 600/424 |
| 2004/0147806 A1 * | 7/2004 | Adler | 600/109 |
| 2005/0085769 A1 * | 4/2005 | MacMahon et al. | 604/96.01 |
| 2005/0273130 A1 * | 12/2005 | Sell | 606/192 |
| 2006/0015126 A1 * | 1/2006 | Sher | 606/159 |

FOREIGN PATENT DOCUMENTS

| | | |
|---|---|---|
| DE | 199 63 161 A1 | 5/2000 |
| EP | 1 230 892 A1 | 8/2002 |
| WO | WO 98/06450 | 2/1998 |
| WO | WO 01/91844 A1 | 12/2001 |
| WO | WO 02/07601 A2 | 1/2002 |

* cited by examiner

*Primary Examiner*—Eric F Winakur
*Assistant Examiner*—Lawrence N Laryea

(57) ABSTRACT

Catheter for insertion into a vessel, comprising a reversibly inflatable balloon (10, 25) provided in the area of the catheter tip, on the outside of which a stent (11) to be implanted in the vessel is arranged, and at least one imaging device (14, 21, 22) arranged in the area of the catheter tip for optical coherence tomography, which is arranged or configured such that the area of the vessel, in which the balloon (10, 25) is positioned, can be captured.

13 Claims, 3 Drawing Sheets

CATHETER FOR INSERTING INTO A VESSEL

CROSS REFERENCE TO RELATED APPLICATIONS

This application claims priority to the German application No. 10 2004 001 498.1, filed Jan. 9, 2004 which is incorporated by reference herein in its entirety.

FIELD OF INVENTION

The invention relates to a catheter for insertion into a vessel, comprising a reversibly inflatable balloon provided in the area of the catheter tip, a stent to be implanted in the vessel being arranged on the outside of said balloon.

BACKGROUND OF INVENTION

One of the most common fatal diseases is vascular disease, in particular cardiac infarct. This is caused by diseases of the coronary arteries, which cause what is known as arteriosclerosis. With such diseases, deposits (atherosclerotic plaque) on the vessel wall cause a reduction in the diameter of the vessel, which can result in the blockage or one or a plurality of coronary arteries. It is now recognized that the risk of cardiac infarct is not primarily due to the reduced vessel diameter. Rather it is a question of whether the thin protective layer covering the arteriosclerotic deposits holds. If it breaks, platelets tend to accumulate at the break, closing the vessel completely within a short time, thereby causing the cardiac infarct. If coronary angiography shows serious narrowing or stenosis in the coronary arteries, causing angina pectoris, associated with restricted performance and a threat to the life of the patient, depending on the individual case either a bypass operation or a balloon dilatation, also known as percutaneous transluminal coronary angioplasty (=PTCA), is carried out. Generally the PTCA procedure is carried out. During this the constrictions in the coronary arteries are widened using a so-called balloon catheter. This catheter has a balloon towards the front of the area of its tip, said balloon generally being of a type that can be inflated with a salt solution and being inflated at the site where the vessel is widened. So that the widened vessel does not return to its original state after dilatation, a so-called stent is inserted into the widened section of the vessel after dilatation. This stent is a cylindrical, generally metal, mesh grid, which is shaped in a plastic manner using the balloon and is held against the inner wall of the vessel.

The usual treatment method first provides for diagnosis of the stenosis by means of a cardiac catheter examination as part of a coronary angiography procedure with contrast agents subject to X-ray control. To this end a catheter is inserted into the coronary vessels and the contrast agent is injected into the coronary vessels via the catheter. The catheter is then removed. The disadvantage of this method step is that only the vessel diameter that can be used by the blood flow or the constriction is shown as a silhouette. No information is available about the deposit, in particular its thickness or the extent of the inflammation process. After the first diagnosis of stenosis, the balloon catheter is inserted subject to X-ray control and the vessel is widened. The catheter is then removed. A further catheter is now inserted to position the stent. This is fed in up to the point of the vessel to be treated, after which the stent is positioned as described by inflating the catheter and the catheter is then removed again. This also takes place under X-ray control, with the disadvantage that the stent cannot easily be seen in the angiography X-ray image, i.e. the possibility of verifying whether the stent has been positioned correctly is very limited.

SUMMARY OF INVENTION

Recently, for more accurate diagnosis of stenosis, an intravascular ultrasound catheter has been inserted into the coronary vessel and then taken out again using a guide wire. The catheter supplies ultrasound images from the coronary vessels and the vessel wall is generally scanned in a 360° image. This method provides important medical information about the deposits and such a catheter can also be used to verify the location of the stent after positioning. One disadvantage is that the ultrasound images only have limited, relatively low resolution. Another disadvantage is that the ultrasound catheter has to be inserted more than once. It is generally a disadvantage that the known procedure requires multiple invasions. In other words a number of different catheters have to be inserted, which is disadvantageous, particularly as each invasion is associated with a certain risk to the patient.

A catheter is known from WO 02/07601 that comprises a balloon with a stent arranged thereon, as well as an ultrasound imaging device. With this catheter it is possible on the one hand to position the stent and on the other hand to capture ultrasound images from the vessel. However one disadvantage here is particularly the relatively low resolution of the ultrasound images captured by this means, with the result that overall the diagnosis result is no more reliable than with the X-ray angiography used to date and so would not justify the high price for the use of this combination catheter.

The invention is therefore intended to resolve the problem of specifying a catheter, which allows the positioning of a stent and the capturing of high-resolution images from the examination and treatment area, in particular control of the positioning and final location of the stent.

To resolve this problem, at least one imaging device provided in the area of the catheter tip is provided in a catheter of the type mentioned above for optical coherence tomography, said imaging device being arranged or configured so that the vessel area in which the balloon is positioned can be captured.

Optical coherence tomography imaging, frequently also referred to as OCT imaging, supplies high-resolution images, which reproduce all the details of the vessel area very precisely, so that there is a clear improvement in the images used for diagnosis. The OCT principle is based on light supplied from the catheter via an optical waveguide being radiated into the vessel, light reflected there being injected back into the optical waveguide and being fed to an evaluation unit, where its coherence with a reference light is evaluated for image generation. The OCT method is adequately known and it is not necessary to examine it further here.

The OCT imaging device is arranged or configured according to the invention such that it can be used to capture the vessel area, in the vicinity of which the balloon with the stent arranged thereon is located. It is thereby possible particularly advantageously to use the OCT imaging device to verify on the one hand when the vessel area to be treated is reached during the insertion movement, as with continuous OCT imaging movement in the vessel can be detected and monitored continuously. It is also possible to position the balloon and catheter with absolute precision, as the OCT imaging device captures with equal precision the area of the vessel in which the balloon and stent are located. This means that the actual position of the balloon can be detected and the balloon can be positioned precisely. Similarly a location and position control can be carried out continuously during and after the fixing of the stent, without having to move or change the catheter in any way. This means that with a single invasion the catheter according to the invention can provide a precise diagnosis of stenosis and well as accurate orientation and positioning of the stent with simultaneous vessel dilatation. The disadvantages mentioned above are therefore advantageously eliminated, as on the one hand high-resolution images that can be evaluated precisely for diagnosis purposes can be captured using OCT imaging and on the other hand the number of invasions and the number of catheters that have to be used is minimized. In the simplest instance only one catheter, namely the OCT balloon-stent catheter according to the invention, has to be used.

In order to be able to capture the vessel area near to the balloon, it is expedient for the imaging device to be arranged essentially in direct proximity to the balloon. It can thereby be arranged in front of or behind the balloon in relation to the catheter tip, if only one imaging device is provided.

An expedient development of the invention provides for the use of two imaging devices operating independently of each other, one of which is arranged in front of and the other behind the balloon, with essentially opposing imaging directions. In other words the vessel wall is captured from two sides, the imaging areas expediently overlapping, so that it is ensured that the entire vessel area treated by means of dilatation and the stent to be positioned is captured in the context of the imaging operation.

As described above, the OCT imaging device comprises an optical waveguide, via which light is supplied from outside, emitted by the catheter, reflected light being injected back and output to the processing device. The optical waveguide can thereby be stationary, i.e. the light is extracted at a defined point on the catheter sheath via a suitable transparent window and captures a defined area of the vessel wall. The optical waveguide does not rotate in this process. In order to capture a 360° image, it would be necessary to rotate the catheter actively. With the catheter according to the invention therefore the imaging device(s) is/are expediently configured with a rotating optical waveguide, to which a circumferential radiation-transparent window provided on the catheter sheath is assigned, via which the radiation can be injected and extracted. In other words the optical waveguide rotates inside the catheter and the light beam scans the vessel wall during rotation. This configuration can expediently be selected for both imaging devices, as long as two are provided. It is of course also possible just to provide one imaging device with a rotating optical waveguide, while the other has a stationary optical waveguide for example and its captured images are only evaluated as control images.

An opening can also be provided in the vicinity of at least one imaging device or at least one window to emit a fluid, in particular a rinsing fluid or a contrast agent, the respective supply line running inside the catheter. According to this embodiment of the invention, the initial diagnosis can also be carried out using the catheter according to the invention in the context of the X-ray angiography, as described in the introduction. In other words when using the catheter according to the invention, this additional invasive examination stage can also be dispensed with.

The stent itself is expediently a so-called drug-eluting stent. With this type of stent, the stent is coated with a drug, which prevents growth in the tissue. Standard uncoated stents are fixed in position in the long term by a growth of vascular tissue around the stent over time once it has been put into position, so that it can be said to grow into place. This is not necessarily desirable, as it is associated with a certain further narrowing of the vessel. This growth is largely prevented when using a drug-eluting stent. Since the growth and scarring of the vessel tissue holding the stent in place are suppressed here, the correct location and positioning of the stent are of particular importance, i.e. the stent has to be fixed in place precisely. This can advantageously be verified with high resolution and precision using ICT imaging.

Either a guide wire or an external guide catheter can be provided to move the catheter, depending on the intended use and configuration. Alternatively it is possible to provide an element to generate the magnetic field for guiding the catheter by means of an external magnetic field in the area of the catheter tip. This can be a permanent magnet or an electromagnet, which is activated via suitable supply lines from outside.

In order to link the catheter simply to the external devices required for its operation or to evaluate the information provided, an interface device is expediently provided at its free end. The control and processing device required for optical coherence tomography can be connected to this on the one hand, as can on the other hand a pump used to inflate the balloon, as well as a supply device for fluid to be emitted if required and also if required a control device to generate the magnetic field. Finally one or a plurality of X-ray opaque markings can be provided in the area of the catheter tip, allowing simple capture of the catheter during X-ray angiography.

BRIEF DESCRIPTION OF THE DRAWINGS

Further advantages, features and details of the invention will emerge from the exemplary embodiments described below and from the drawings, in which.

DETAILED DESCRIPTION OF INVENTION

Figure 1:
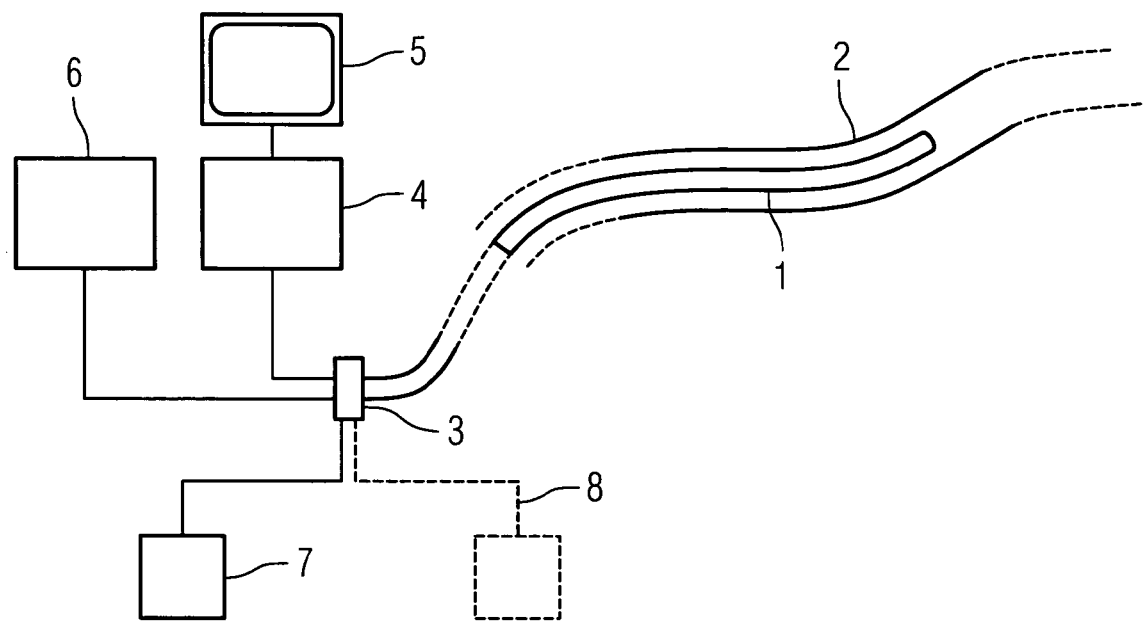
FIG. 1 shows an outline diagram of the catheter according to the invention along with assigned devices.

FIG. 1 shows an outline diagram of a catheter 1 according to the invention inserted into a vessel 2. The end of the catheter 1 that is not inserted is connected via an interface device 3 on the one hand to a control and processing device 4 as part of the OCT imaging system. Inside the catheter is an OCT imaging device comprising an optical waveguide, which will be examined in more detail below. Light is supplied via the control and processing device 4 to the integrated optical waveguide and light coming from the optical waveguide is captured and processed, to generate high-resolution OCT images, which are output to a monitor 5.

Also connected to the interface device 3 is a pump 6, by means of which a balloon provided at the catheter tip, which is used both for dilatation and for widening and positioning the stent, can be inflated.

Also connected to the interface device 3 is a fluid pump 7, via which rinsing fluid or a contrast agent are fed into the catheter and can be output via an opening on the catheter. As an option (and therefore shown with a broken line) a magnetic field generating device 8 can be provided at the interface device 3, which can be used to activate an electromagnet, which can be provided at the catheter tip, to generate a magnetic field.

Figure 2:
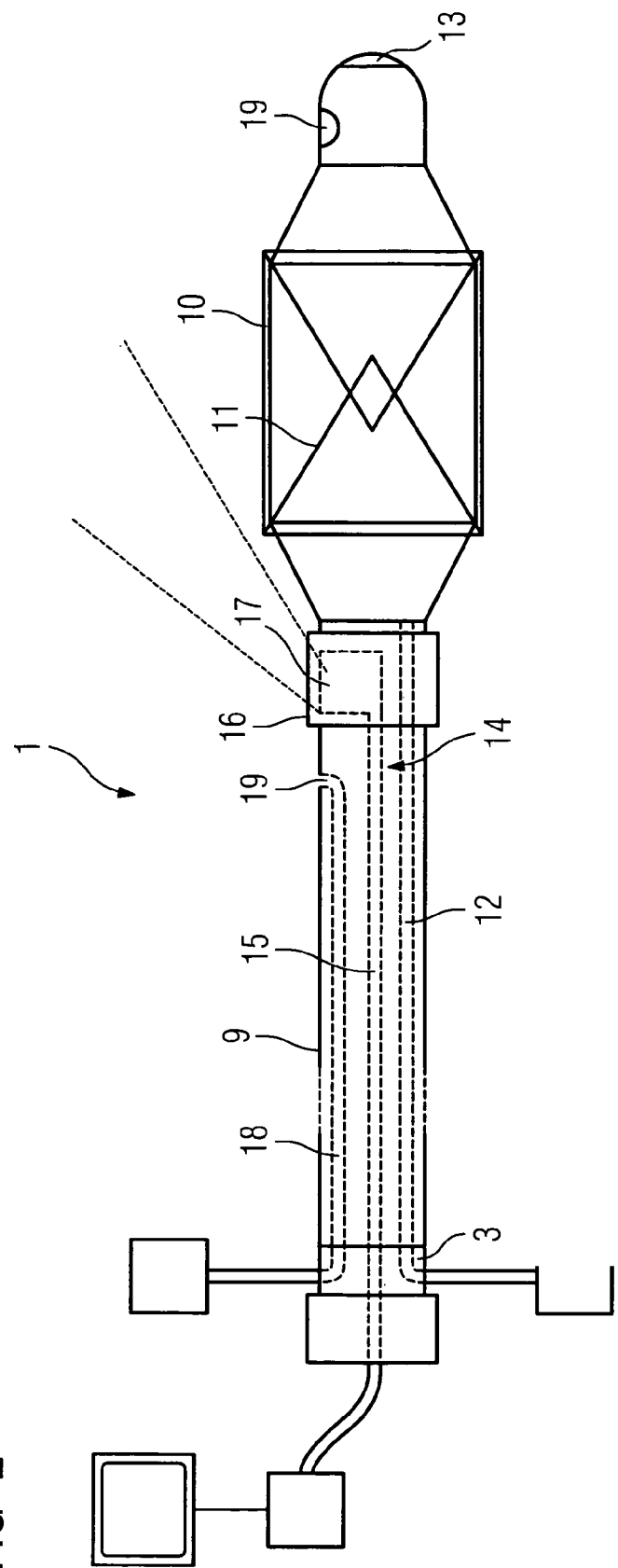
FIG. 2 shows an enlarged view of an outline diagram of the catheter according to the invention in a first embodiment and FIG. 3 shows a partial view of a catheter according to the invention in the form of an outline diagram according to a second embodiment.

FIG. 2 shows an outline diagram of the catheter 1 known from FIG. 1. It comprises a catheter sheath 9, also a balloon 10 provided in the area of the catheter tip, on the outside of which a stent 11, primarily a drug-eluting stent is arranged. The balloon 10 can be linked via a gas or fluid supply line 12 to the pump already described above by means of the interface device 3.

A magnetic field generating element 13 is also provided at the catheter tip, which can be a permanent magnet or an electromagnet that can be activated by means of the magnetic field generating device 8.

An OCT imaging device 14 is also provided, comprising an optical waveguide 15, which runs from the interface device 3, at which it can be linked to the control and processing device 4, along the inside of the catheter to the area of a radiation-transparent window 16, via which the light supplied by the optical waveguide, generated by means of a suitable illumination device in the control and processing device 4, is emitted, to illuminate the section of the vessel wall, and injected back into the optical waveguide 15 via the corresponding reflected light and fed to the control and processing device 4 to generate an image. A light distribution element 17 is provided in the area of the window 16, which ensures that the emitted light is radiated outward in such a manner that the area of the vessel wall opposite the balloon 10 can be scanned and captured and the reflected light originating from this area can be injected. The optical waveguide 15 and where applicable the light distributor 17 too rotate so that 360° all-round images can be captured.

Finally a further line 18 is provided, which opens into an opening 19 on the catheter sheath and which can be linked via the interface device 3 to the fluid pump 7 described above. This can be used to supply contrast agent or rinsing fluid.

During operation the catheter 1 is inserted into the vessel subject to X-ray control, with one or a plurality of X-ray opaque markings 19 provided primarily in the area of the tip for control purposes. This may be effected with the administration of contrast agent via the opening 19. Once the required target position is reached, the rinsing fluid is injected in via the line 18, so that for a short time the blood in the area of the vessel is washed away and the stenosis or vessel wall can be observed at high resolution with the OCT imaging device 14. This allows information to be obtained about the stenosis and also allows the positioning of the balloon 10 and with it the stent 11 to be verified. If it proves that the positioning is not correct, the catheter can easily be moved further forward or pulled back, until the balloon 10/stent 11 is correctly positioned. This is all possible, because the imaging device 14 allows the area of the vessel immediately opposite the balloon 10/stent 11 to be captured. If the balloon/stent is correctly positioned, the balloon 10 is inflated using the pump 6, using air or primarily a common salt solution. The balloon 10 is extended in a defined manner and the stent 11, which is generally a metal grid that can be deformed in a plastic manner, is similarly extended. The balloon is thereby inflated until the stent is so to speak held in position on the inner wall of the vessel. The balloon is then deflated slightly so that the position and location of the stent can be verified using the OCT imaging device 14. If it proves that the stent is correctly positioned, the balloon is once again inflated to a higher pressure and the stent is finally fixed in position. The balloon is deflated again so that a final verification can be made via the OCT imaging device 14, after which the catheter is removed.

Figure 3:
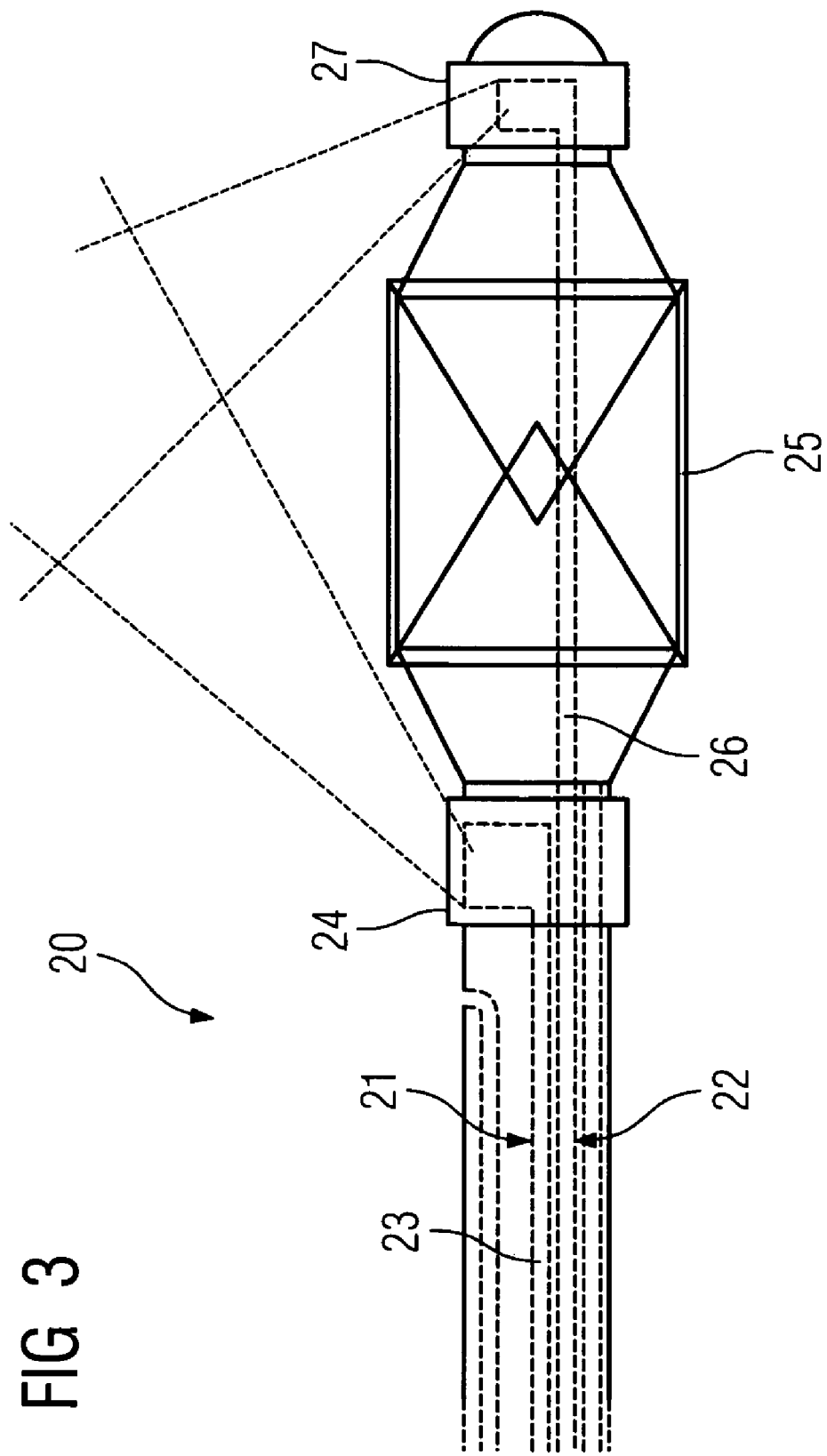

FIG. 3 shows a further embodiment according to the invention of a catheter 20, the basic structure and interface options of which correspond essentially to those of the catheter 1 in FIG. 2. However here two OCT imaging devices 21, 22 are provided, allowing the imaging of the vessel wall from two different directions. The OCT imaging device 21 corresponds to the imaging device 14 in FIG. 2 and is designed correspondingly. An optical waveguide 23 is provided here too, as is a window 24, from which or into which the light is injected. This imaging device is arranged in front of the balloon 25 in relation to the recording point in the direction of the catheter tip. The second OCT imaging device 22 also comprises an optical waveguide 26, which is fed through the balloon 25 via suitable, if necessary lined, guide openings. The assigned beam inlet and outlet window 27 is located in front of the balloon 25 in the direction of the catheter tip. As shown, the recording directions of the two imaging devices are almost opposing, so that the area of the vessel wall is captured from both sides with the imaging areas overlapping, as shown.

Both optical waveguides 23, 26 preferably rotate but it is also possible for the optical waveguide 26 to be fixed and to be used solely to capture a control image in addition to the rotating image of the imaging device 21.

Both optical waveguides 23, 26 can be "operated" via a common control and processing device 4. Separate controllers are also of course possible.

The invention claimed is:

1. A catheter for inserting into a vessel, comprising:
   a reversibly inflatable balloon arranged at a tip of the catheter for dilatation of a portion of the vessel such that a stent may be inserted into a resulting widened region;
   a stent for implanting into an inner area corresponding to the widened region of the vessel, the stent arranged on the outside of the balloon; and
   an imaging device for optical coherence tomography, the imaging device operatively connected to the balloon and configured to capture an image of the inner area,
   further comprising a further imaging device configured to operate independently from the imaging device, wherein the imaging device is arranged upstream from the balloon and the further imaging device is arranged downstream from the balloon relative to the tip, the imaging and further imaging devices having opposing image capturing directions.

2. The catheter according to claim 1, wherein the imaging device comprises:
   a rotatable optical fiber arranged inside the catheter for capturing 360° all-round images; and
   a radiation-transparent window arranged on a jacket of the catheter for injecting and extracting radiation.

3. The catheter according to claim 1, wherein the further imaging device comprises:
   a further rotatable optical fiber arranged inside the catheter for capturing 360° all-round images; and
   a further radiation-transparent window arranged on a jacket of the catheter for injecting and extracting radiation.

4. The catheter according to claim 1, further comprising an opening for emitting a fluid fed to the catheter.

5. The catheter according to claim 1, wherein the stent is a drug-eluting stent.

6. The catheter according to claim 1, further comprising a guide wire or an external guide catheter for navigating the catheter.

7. The catheter according to claim 1, further comprising a magnetic navigation element arranged at the tip and configured to generate a magnetic field for navigating the catheter using an external magnetic field.

8. The catheter according to claim 1, further comprising an interface device arranged at a catheter end, the interface device configured to:

connect to the catheter a control and processing device, the control and processing device adapted to control the imaging device, and connect to the catheter a pump for inflating the balloon.

9. The catheter according to claim 8, wherein the interface device is further configured to connect to the catheter a supply device for supplying a fluid to the catheter.

10. The catheter according to claim 8, wherein the interface device is further configured to connect to the catheter a navigation control device for generating a magnetic field at the catheter tip, the magnetic field used for navigating the catheter.

11. The catheter according to claim 1, further comprising at least one X-ray opaque marking arranged at the tip.

12. A catheter for inserting into a vessel, comprising:
a reversibly inflatable balloon arranged at a tip of the catheter for dilatation of a portion of the vessel such that a stent may be inserted into a resulting widened region;
a stent for implanting into an inner area corresponding to the widened region of the vessel, the stent arranged on the outside of the balloon; and
an imaging device for optical coherence tomography, the imaging device operatively connected to the balloon and configured to capture an image of the inner area, further comprising a further imaging device configured to operate independently from the imaging device, wherein the imaging device is arranged downstream from the balloon and the further imaging device is arranged upstream from the balloon relative to the tip, the imaging and further imaging devices having opposing image capturing directions.

13. The catheter according to claim 12, wherein the further imaging device comprises:
a further rotatable optical fiber arranged inside the catheter for capturing 360° all-round images; and
a further radiation-transparent window arranged on a jacket of the catheter for injecting and extracting radiation.

* * * * *